United States Patent
Calasso et al.

(10) Patent No.: US 7,959,581 B2
(45) Date of Patent: Jun. 14, 2011

(54) TEST MAGAZINE AND METHOD FOR PROCESSING THE SAME

(75) Inventors: Irio G. Calasso, Arth (CH); Martin Kopp, Hagendorn (CH); Charles Raney, Camdenton, MO (US); Steven N. Roe, San Mateo, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 204 days.

(21) Appl. No.: 11/537,791

(22) Filed: Oct. 2, 2006

(65) Prior Publication Data

US 2007/0038150 A1    Feb. 15, 2007

Related U.S. Application Data

(63) Continuation of application No. PCT/EP2005/004646, filed on Apr. 29, 2005, which is a continuation-in-part of application No. 10/836,578, filed on Apr. 30, 2004.

(51) Int. Cl.
| | |
|---|---|
| *A61B 5/00* | (2006.01) |
| *A61B 17/14* | (2006.01) |
| *A61B 17/32* | (2006.01) |
| *B65D 81/00* | (2006.01) |
| *G01N 21/00* | (2006.01) |
| *G01N 31/00* | (2006.01) |
| *G01N 33/00* | (2006.01) |
| *G01N 35/00* | (2006.01) |

(52) U.S. Cl. ........ 600/583; 600/575; 600/576; 600/584; 606/181; 422/66; 436/44

(58) Field of Classification Search .......... 600/573–584; 606/181; 422/66; 436/44
See application file for complete search history.

(56) References Cited

U.S. PATENT DOCUMENTS

| | | |
|---|---|---|
| 2,989,212 A | 6/1961 | Ekenstam et al. |
| 3,039,652 A | 6/1962 | Ekenstam et al. |
| 3,526,480 A | 9/1970 | Findl et al. |
| 3,620,678 A | 11/1971 | Guigan et al. |
| 3,786,510 A | 1/1974 | Hodges |
| 3,835,992 A | 9/1974 | Adams, IV |
| 4,123,840 A | 11/1978 | Rumer, Jr. |

(Continued)

FOREIGN PATENT DOCUMENTS

DE     2803345 B1     6/1979

(Continued)

OTHER PUBLICATIONS

U.S. Appl. No. 10/836,578 Office Action mailed Aug. 14, 2009.

(Continued)

*Primary Examiner* — Max Hindenburg
*Assistant Examiner* — John Pani
(74) *Attorney, Agent, or Firm* — Woodard, Emhardt, Moriarty, McNett & Henry LLP

(57) ABSTRACT

A test magazine with two film strips (12, 14), which are joined to one another in a sandwich-like manner, can be wound up, and between which holding cells (16) for test elements are kept free. The test magazine also comprises a multitude of test elements (18, 20) each having a puncturing unit (18) for inserting into body tissue and a test unit (20) for being subjected to body fluid. To this end, the puncturing units (18) and test units (20) are placed in separate holding cells (16) whereby separating them from one another.

34 Claims, 3 Drawing Sheets

U.S. PATENT DOCUMENTS

| | | | |
|---|---|---|---|
| 4,218,421 A | 8/1980 | Mack, Jr. et al. | |
| 4,328,184 A * | 5/1982 | Kondo | 422/58 |
| 4,883,642 A | 11/1989 | Bisconte | |
| 4,995,402 A | 2/1991 | Smith et al. | |
| 5,047,044 A | 9/1991 | Smith et al. | |
| 5,077,010 A | 12/1991 | Ishizaka et al. | |
| 5,096,828 A | 3/1992 | Ishizaka et al. | |
| 5,178,835 A | 1/1993 | Uekusa et al. | |
| 5,228,972 A | 7/1993 | Osaka et al. | |
| 5,679,311 A | 10/1997 | Harttig et al. | |
| 5,686,829 A | 11/1997 | Girault | |
| 5,997,817 A | 12/1999 | Crismore et al. | |
| 6,488,891 B2 | 12/2002 | Mason et al. | |
| 6,887,709 B2 | 5/2005 | Leong | |
| 2002/0052618 A1 | 5/2002 | Haar et al. | |
| 2002/0076349 A1 | 6/2002 | Aitken et al. | |
| 2002/0076357 A1 | 6/2002 | Hahs et al. | |
| 2002/0188224 A1 | 12/2002 | Roe et al. | |
| 2003/0050573 A1* | 3/2003 | Kuhr et al. | 600/567 |
| 2003/0083685 A1 | 5/2003 | Freeman et al. | |
| 2003/0171699 A1 | 9/2003 | Brenneman | |
| 2003/0199789 A1* | 10/2003 | Boecker et al. | 600/575 |
| 2003/0199904 A1 | 10/2003 | Boecker et al. | |
| 2003/0211619 A1* | 11/2003 | Olson et al. | 436/44 |
| 2003/0212344 A1 | 11/2003 | Yuzhakov et al. | |
| 2004/0120848 A1 | 6/2004 | Teodorczyk | |
| 2004/0138688 A1 | 7/2004 | Giraud | |
| 2005/0021066 A1 | 1/2005 | Kuhr et al. | |
| 2005/0149088 A1 | 7/2005 | Fukuda et al. | |
| 2005/0232815 A1* | 10/2005 | Ruhl et al. | 422/66 |
| 2005/0245845 A1 | 11/2005 | Roe et al. | |
| 2005/0245954 A1 | 11/2005 | Roe et al. | |
| 2006/0200045 A1 | 9/2006 | Roe | |

FOREIGN PATENT DOCUMENTS

| | | |
|---|---|---|
| DE | 19819407 A1 | 11/1999 |
| DE | 19849539 A1 | 5/2000 |
| DE | 19857426 A1 | 6/2000 |
| EP | 0637749 A2 | 2/1995 |
| EP | 1203563 A2 | 5/2002 |
| EP | 1321769 A1 | 6/2003 |
| EP | 1360935 A1 | 11/2003 |
| JP | 1105157 A1 | 4/1989 |
| JP | 05-010951 | 1/1993 |
| JP | 5045363 A1 | 2/1993 |
| WO | WO93/09710 A1 | 5/1993 |
| WO | WO02/18940 A2 | 3/2002 |
| WO | WO03/082092 A1 | 10/2003 |
| WO | WO2004/060174 A2 | 7/2004 |
| WO | WO2005/104948 A1 | 11/2005 |
| WO | WO 2007/147494 A2 | 12/2007 |

OTHER PUBLICATIONS

U.S. Appl. No. 11/105,686 Office Action mailed Sep. 3, 2009.

Priebs, Hendrik. "Test Strip Container for Measurement Devices which Operate with a One-Way Test Strip". Nov. 11, 1999. Certified translation of DE 19819407 produced Feb. 2011 by Schreiber Translations, Inc.

* cited by examiner

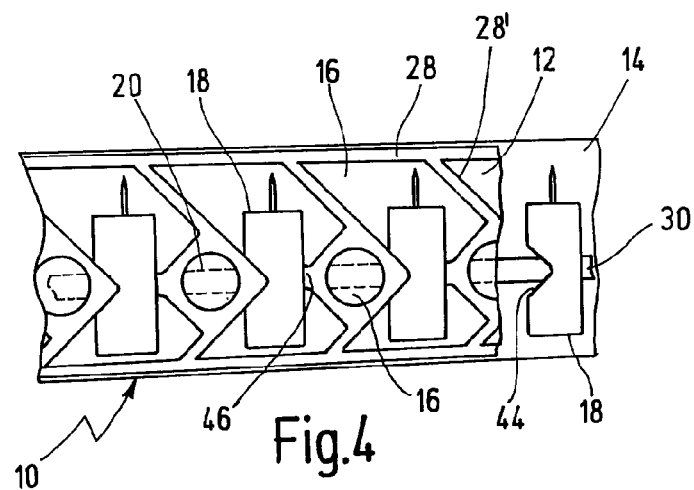
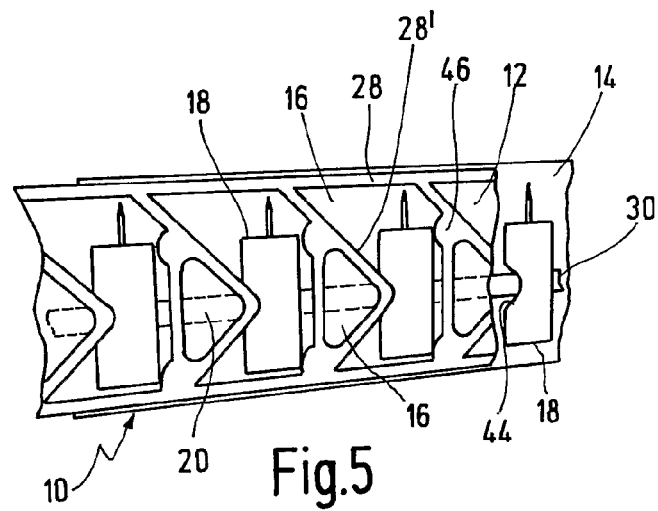
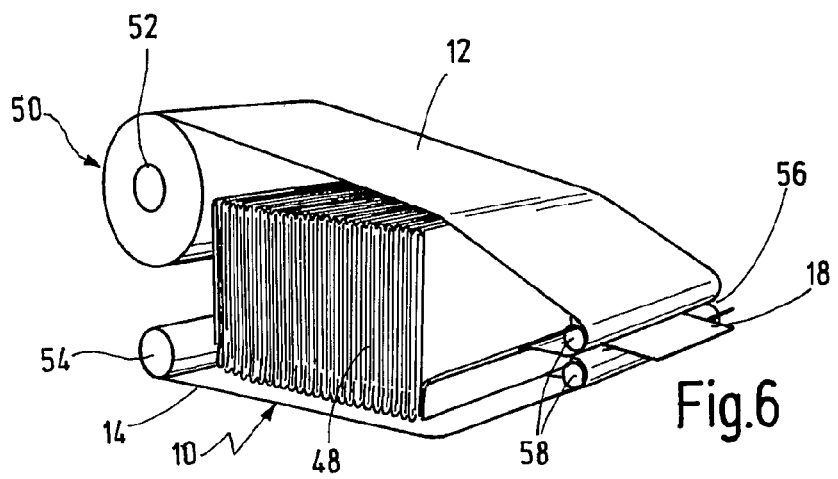

TEST MAGAZINE AND METHOD FOR PROCESSING THE SAME

CROSS REFERENCE TO RELATED APPLICATIONS

This application is a continuation of International Application No. PCT/EP2005/004646 filed Apr. 29, 2005, which is a continuation-in-part of U.S. application Ser. No. 10/836,578 filed Apr. 30, 2004, which are hereby incorporated by reference.

BACKGROUND

The invention concerns a test magazine comprising two spoolable foil tapes that are joined together in a sandwich-like manner and between which holding cells for test elements are kept free, and a plurality of test elements which each comprise a lancing unit for piercing body tissue and a test unit to which body fluid can be applied. The invention also concerns a method for processing such a magazine.

Such test systems are intended for use especially by diabetics for blood sugar self-monitoring that is carried out several times daily. Recent concepts envisage a microneedle in conjunction with a test field as a single-use system (disposable) in order to generate a skin puncture, to utilize capillary forces to remove a small amount of blood therefrom and to analyse this blood sample. Such an integrated system should also enable laymen to carry out the required steps in a simple and rapid manner in a substantially automated measuring process. An important aspect is miniaturization also with regard to a high integration of disposables in a small space in a portable device. In this connection blister packs for test elements integrated into a firm package have already been proposed which, however, due to a rigid framework with well-shaped mouldings have disadvantages for the manufacture as well as in use.

On this basis the object of the invention is to avoid the disadvantages that occur in the prior art and to make improvements which also enable a high integration density and hygienic handling.

SUMMARY

The combinations of features stated in the independent patent claims are proposed to achieve this object. Advantageous embodiments and further developments of the invention are derived from the dependent claims.

The idea behind the invention is to ensure a high integration density and handling safety for test elements in two-dimensional cell-shaped regions of a foil pack. Accordingly a first aspect of the invention is that the lancing units and test units are arranged separately from one another in separate holding cells. The cells can be simply provided by the intermediate region between the foil tapes that are not further formed out. The separation is also advantageous with regard to the fact that the lancing elements can be independently pretreated and in particular sterilized and hydrophilized without damaging the test chemistry and there is no risk during the lancing process that test chemicals enter the body. Moreover, this solution is characterized by the possibility of a simple manufacture in particular by roll-to-roll manufacture which enables a particularly flat, spoolable construction.

The lancing units and test units are advantageously arranged alternately in the tape direction or adjacent to one another in pairs at right angles to the tape direction in assigned holding cells.

A particularly preferred embodiment provides that the lancing units in the assigned holding cells are sterilized by irradiation preferably through a mask in order to screen the test units.

The manufacture can also be simplified by means of the fact that the foil tapes are joined to a test tape over their length and that cells on the test tape are exposed by perforations in the foil tape to form the test units.

With regard to a long shelf-life it is also advantageous when a desiccant for the test units is stored in the holding cells.

Another aspect of the invention is that at least the lancing units can be removed by transport means from their respective holding cell and can be moved into a working position which is completely separate from the foil tapes. This enables a completely automated processing sequence that is unimpeded by the storage in magazines which also allows the hygienic disposal of used units in a simple manner.

In order to simply and successively expose individual units, it is advantageous when the transport means comprises a tape tensioning device to pull apart the foil tapes in different directions. This can be achieved by the tape tensioning device having two deflecting cylinders that can rotate in opposite directions or are stationary and are arranged laterally spaced apart from one another at a dispensing site, and having tape-up spools for the foil tapes downstream of the deflecting cylinders.

In order that the body fluid to be analysed after the collection process can be further processed in a simple manner, it is advantageous when the transport means are in operative connection with a test unit and/or disposal site located on the foil tape in order to return a lancing unit.

Another improvement is achieved by the transport means having a handling device to pick up and position a lancing unit that has been exposed by pulling apart the foil tape at a dispensing position. In this connection it is advantageous when at least one of the foil tapes has positioning holes especially in the region of the holding cells for the test units to enable the handling device to engage.

The individual removal and handling is also suitable for integrated test elements in which the lancing units are physically joined to the test units.

A particularly preferred embodiment of the invention provides that at least one of the foil tapes is provided with a withdrawal structure for the preferably adhesive or clamping fixation of used lancing elements. This enables a particularly simple disposal of contaminated units.

In order to increase the integration density it is advantageous when the lancing units are arranged flat between the foil tapes as flat material components. In this case the foil tapes should have a planar design and rest laminarly against the lancing units free of blisters or three-dimensional mouldings.

Another advantageous embodiment provides that the lancing units exposed at a dispensing site can be redispensed at a return position on one of the foil tapes that is distant thereto. This additionally avoids limitations in the individual handling of lancing units and test elements that may be joined thereto.

The lancing units advantageously have a capillary structure that is preferably formed by a semi-open channel to collect body fluids. Another improvement provides that the lancing units are formed on the test units in order to transfer collected body fluid.

For the manufacture of the cell structure it is advantageous when the holding cells are delimited by linear foil connections, preferably welded or adhesive seams between the foil tapes. Another improvement is achieved in that the holding cells are sealed against the environment in a material-tight manner by the foil connections.

In order to make it easy to tear open the foil pack, it is advantageous when the linear foil connections extend obliquely to the tape longitudinal direction of the foil tapes.

The lancing units are advantageously immobilized in a fixed position in their assigned holding cell by form-locking bordering foil connections or foil connections that engage in recesses.

It is also advantageous when at least one of the foil tapes has or forms a transparent measuring window for an optical measurement of the test units to enable a contact-free scanning through the tape.

A high packaging density can also be achieved in that the foil tapes with the test elements located therein are held ready as a folded package in a zigzag folding.

The foil tapes with test elements located therein are advantageously accommodated in a cassette.

The test units can be specially designed as detection fields coated with reagents to detect an analyte in the body fluid and in particular glucose.

The invention also concerns a test device for processing a said test magazine.

With regard to the process the object stated above is achieved in that the lancing units optionally in conjunction with integrated test units are individually exposed by pulling apart the foil tapes, are then moved into a working position that is distant from the associated holding cell and are subsequently stored again on one of the foil tapes. In this connection it is particularly advantageous when body fluid is collected in the working position by means of the lancing units and is subsequently transferred onto the test units.

The invention is elucidated in more detail in the following on the basis of the embodiment examples shown schematically in the drawing.

BRIEF DESCRIPTION OF THE DRAWINGS

FIGS. 4 and 5 show further embodiments of foil magazines in a sectional top-view.

FIG. 6 shows an embodiment with a bellows as a store for test elements in a diagrammatic view.

DESCRIPTION OF THE SELECTED EMBODIMENTS

Figure 1:
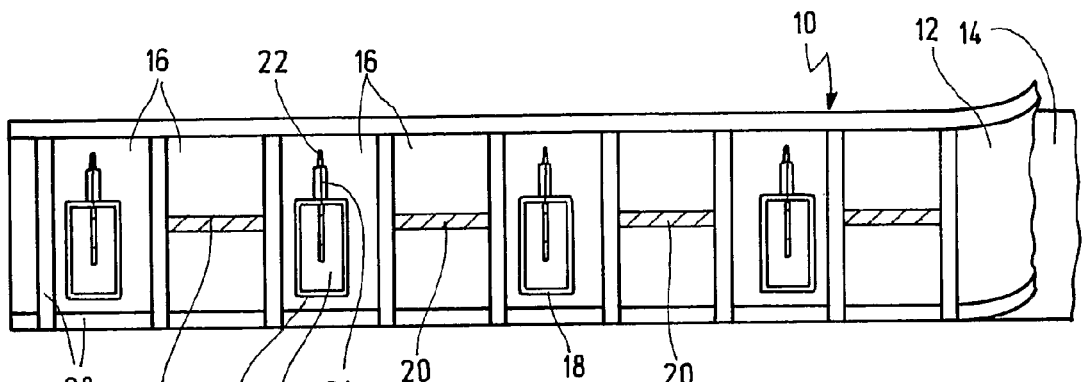
FIG. 1 shows a foil magazine for blood glucose tests in a sectional top-view.

The test magazines shown in the drawing comprise as a foil package 10, two foil tapes 12, 14 which are joined together in a sandwich-like manner and between which holding regions or cells 16 are kept free in which test elements 18, 20 are made available for successive processing.

As shown in FIG. 1 lancing units 18 and test units 20 arranged in pairs are provided as test elements which are arranged separately from one another in separate holding cells 16. In the embodiment examples shown the lancing units 18 and test units 20 are arranged alternately in the direction of the tape. They may also conceivably be arranged at the side of one another at right angles to the tape direction or obliquely displaced or be present as integrated combinations of test elements in which the lancing units 18 are physically joined to the test units 20.

The lancing units 18 are formed from a thin sheet of high-grade steel as flat formed parts and have a distal lancing member 22 in the form of a microneedle to puncture for example the finger of a test person for blood collection. The lancing member 22 is connected via a semi-open groove-shaped capillary channel 24 to a holding region 26 to collect and transfer blood. For this purpose the respective lancing unit 18 is connected after the collection process with an associated test unit 20 in such a manner that the collected blood is applied to this test unit in order to detect an analyte (glucose) located therein in a single measurement. It can be detected in a known manner by means of a colour reaction of the strip-shaped test units 20 and a photometric measurement. For this purpose at least one of the foil tapes 12, 14 can be composed of a transparent material as an optical window.

The holding cells 16 are kept free as essentially two-dimensional expanded intermediate regions between the flat foil tapes 12, 14 in order to receive the test elements 18, 20 in a flat manner. The foil tapes 12, 14 thus rest in a planar manner against the flat test elements free of blisters or of well-shaped mouldings thus enabling a compact winding or space-saving folding. For example the lancing units 18 can have a square measure of 5×10 mm so that even with about 100 units the spool diameter is still acceptable for use in a portable device.

In order to insulate and optionally fix the test elements the holding cells 16 are delimited by linear connections 28 between the foil tapes 12, 14. In FIG. 1 a ladder-shaped structure of welded or adhesive seams is provided for this purpose which ensure a material-tight sealing of the holding cells 16 from one another and from the environment.

The separate arrangement enables the packaged lancing units 18 to be sterilized by irradiation independently of the test units 20 without damaging the sensitive test chemicals of the test units.

This can be carried out by a screening mask that is not shown which allows an energy-rich radiation (X-ray or electron rays) only to pass through to the lancing units 18. In addition the separation enables the lancing units 18 to be hydrophilized by a surface treatment for an effective uptake of liquid without having to make allowances for the test chemistry. Another advantage is that the chemicals used for the detection cannot enter the body of the person being examined during the lancing process.

Figure 2:
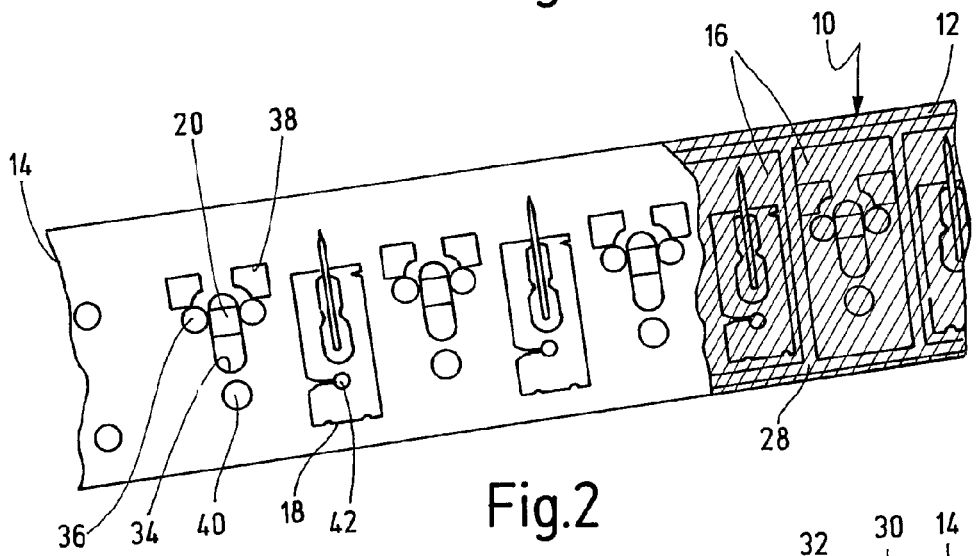
FIG. 2 shows another foil or test magazine in a sectional top-view.
Figure 3:
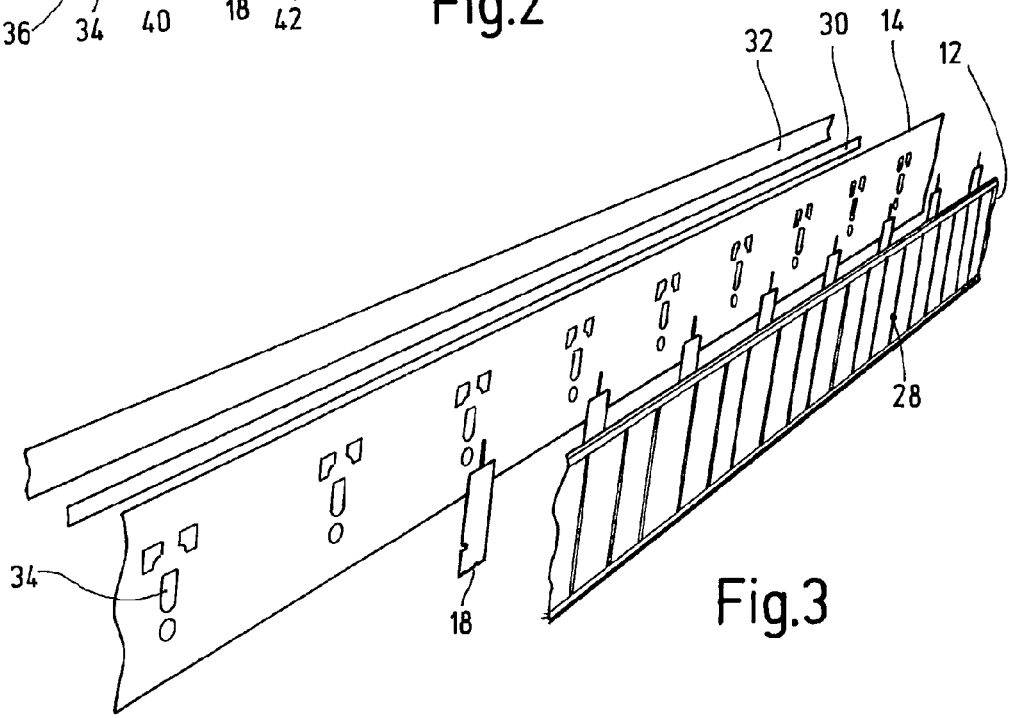
FIG. 3 shows the individual constructional elements of the foil magazine of FIG. 2 in an exploded view.

FIGS. 2 and 3 result in an expedient assembly of a tape package 10 with alternating lancing and test units 18, 20. The prefabricated lancing units 18 are enclosed in a flat manner between the tapes 12, 14 whereby the adhesive lines 18 arranged on the inner side of the tape 12 delimit the holding cells 16. A continuous test strip 30 is fixed by means of an adhesive tape 32 to the outside of the tape 14. The test strip 30 is exposed in each second holding cell 16 by perforations 34 in the carrier tape 14 for applying body fluid or blood such that the separate test units 20 are thus formed. The described multifoil structure simplifies mass production at a high throughput from roll to roll.

Desiccants 36 which are optionally also in the form of tape sections can be contained in the cell regions of the test units 20. Positioning holes 38 are also punched into the tape 14 in these regions in order that the lancing unit 18 can be accurately positioned after the collection process as is elucidated in more detail below. It is particularly advantageous when in particular line-shaped or point-shaped adhesive structures 40 on one of the foil tapes 14 allow a simple restorage of used lancing units 18 or integrated test elements. It is also possible that additional locking points 42 are provided in the cells of the lancing units 18 in order to hold them in a detachable manner.

The embodiments according to FIGS. 4 and 5 show similar foil packages 10 in which the same components are provided with the same reference numerals as described above. In this case the connecting structure 28 between the tapes 12, 14 whose broad sides rest against one another are characterized by additional functions. On the one hand an immobilization of the lancing units 18 is ensured by an engagement in recesses 44 of the lancing units and an abutment of the edge against supporting sites 46. On the other hand, joining seams 28' extending obliquely to the longitudinal direction of the tape enable the tapes 12, 14 to be torn apart to expose the lancing units 18 without peak forces and without jerking.

FIG. 6 illustrates in a very simplified schematic manner the provision of individual test elements or lancing units 18 from the foil magazine 10. In the embodiment shown the foil tapes 12, 14 with the test elements located therein are stored in a zigzag shape as a folded package 48. In order to successively release the lancing units 18, a tape tensioning device 50 is provided in a housing (not shown) which comprises two winding spools 52, 54 for the foil tapes 12, 14 and, in front of them, deflection rollers 58 arranged laterally spaced apart at a dispensing site 56. The lancing units 18 are released for further processing by tearing apart the tapes 12, 14 in the region of the deflection rollers 58. The rotation of the winding spools 52, 54 is synchronized in order to always keep the tapes 12, 14 tensioned. Such an arrangement as a dispenser can also be designed to dispense individual units 18 which are then for example used manually in a separate measuring instrument.

Figure 7:
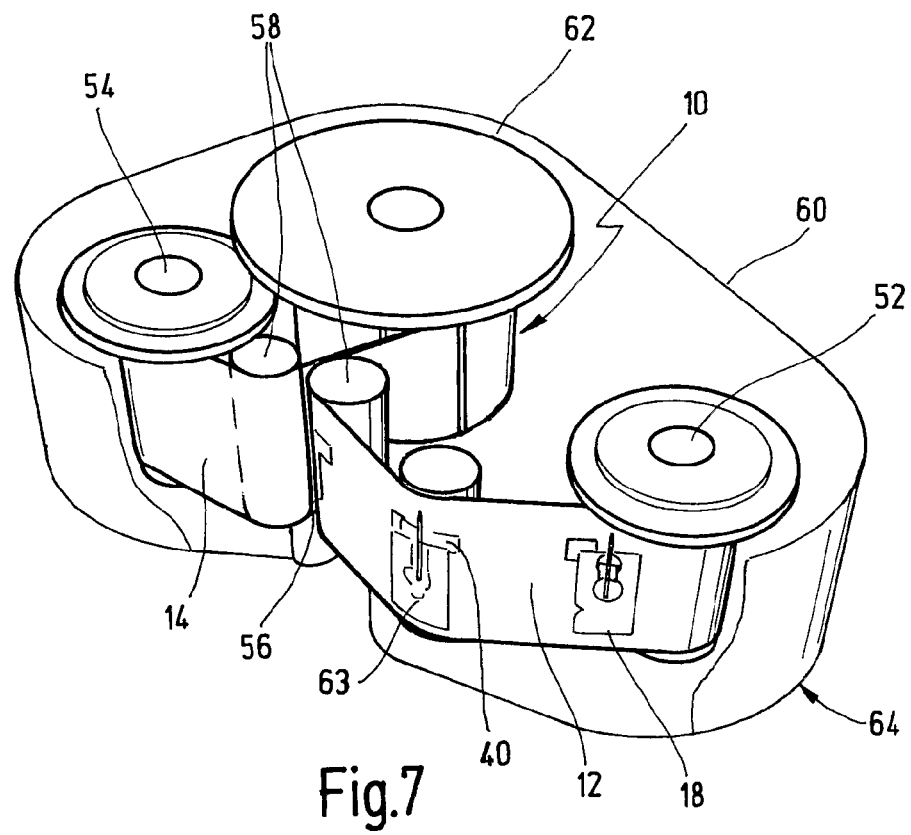
FIG. 7 shows a test magazine in a magazine housing in a broken-open perspective view.

FIG. 7 shows a preferred arrangement in a magazine housing 60 which is shown in a partially broken open view. The foil package 10 is arranged there on a storage roller 62 from which the connected tapes 12, 14 are pulled over the deflection rollers 58 and are thus torn apart to release the test elements. After use the test elements are returned to the inner side of the tape 12 at a return position 63 which is optionally at a distance from the dispensing position 56 where adhesive strips 40 effect the retention. In this manner the used test elements 18 can be wound onto the spool 52 and thus be simply disposed of.

Figure 8:
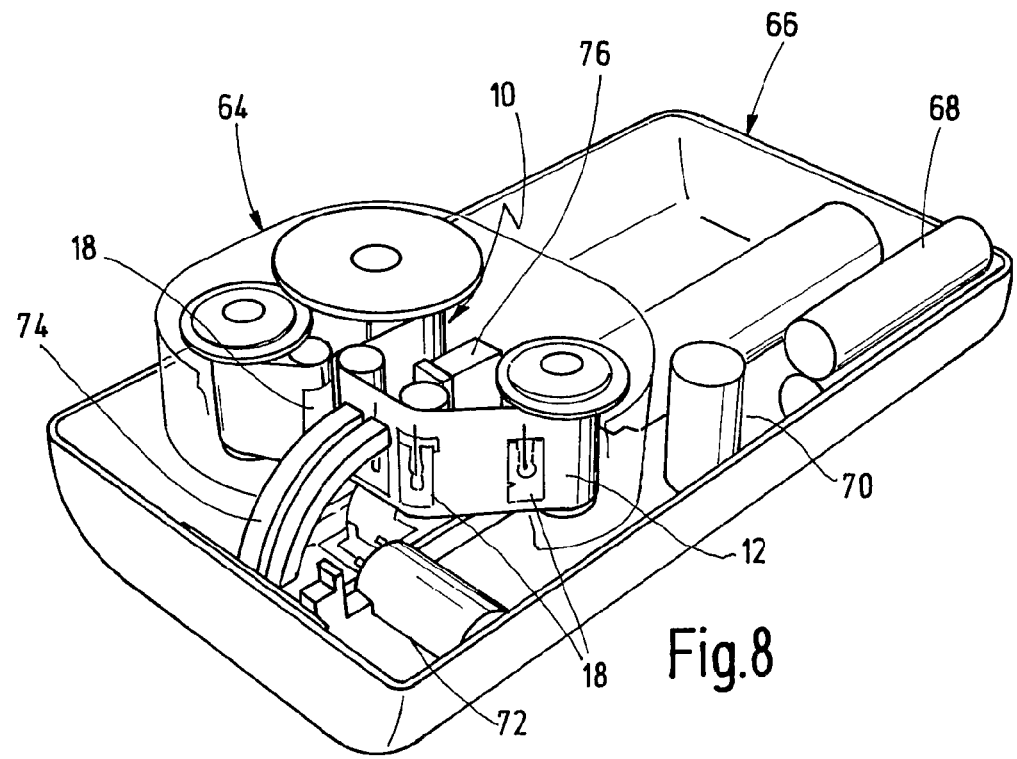
FIG. 8 shows a portable device for processing a test magazine according to FIG. 7.

The test cassette 64 described above can be used in a portable device 66 as a disposable article as shown in a simplified form in FIG. 8. Such a device 66 comprises all equipment required to carry out a glucose measurement such as an energy supply 68, measurement and display electronics 70 and actuatorics 72 for handling individual lancing units 18 dispensed from the tape magazine 10 and measuring optics 76. In the embodiment shown a handling device 74 is provided as part of the actuatorics 72 in order to receive the elements 18 at the dispensing site 56, to move them into a transversely positioned lancing position at a distance from the tapes 12, 14, to carry out the lancing movement through an opening in the housing and to return them onto the tape 12 after blood collection. At this position a contact-free optical measurement is carried out by the measuring unit 76 in order to subsequently be able to display the determined results to the user. In this manner it is possible for laymen to carry out self examinations in a completely automated measuring process whereby the storage magazine allows a large number of tests to be carried out. The used cassettes 64 can be removed as a complete unit from the device 66 without having to individually dispose of the components that are contaminated with blood.

The invention claimed is:

1. A test magazine comprising:
   two spoolable foils joined together in a layered manner and between which holding cells are formed for holding test elements;
   a plurality of test elements which each comprise a lancing unit for puncturing body tissue and a test unit to which body fluid can be applied
   wherein the lancing units and test units are arranged separately from one another in separate holding cells;
   wherein the holding cells are separately sealed from one another;
   wherein the holding cells containing the test units do not contain the lancing units; and
   wherein the lancing units have a capillary structure that is formed by a semi-open channel to collect body fluid.

2. The test magazine of claim 1, characterized in that the lancing units and test units are arranged alternately in a tape direction or adjacent to one another in pairs at right angles to the tape direction.

3. The test magazine of claim 1, characterized in that the lancing units in the holding cells were sterilized by irradiation through a mask in order to screen the test units.

4. The test magazine of claim 1, characterized in that the foils are joined to a test tape over their length and that cells on the test tape are exposed by perforations in the foils to form the test units.

5. The test magazine of claim 1, characterized in that a desiccant for the test units is stored in the holding cells.

6. A test magazine comprising:
   two spoolable foil tapes joined together in a layered manner and between which holding cells are formed for holding test elements;
   and a plurality of test elements arranged in the holding cells, wherein the test elements each comprise a lancing unit for puncturing body tissue and a test unit to which body fluid can be applied;
   wherein at least the lancing units can be removed by transport means from their respective holding cell and can be moved into a working position which is completely separate from the foil tapes;
   wherein the holding cells are separately sealed from one another;
   wherein the holding cells containing the test units do not contain the lancing units; and
   wherein the lancing units have a capillary structure that is formed by a semi-open channel to collect body fluid.

7. The test magazine of claim 6, further comprising:
   the transport means, wherein the transport means comprises a tape tensioning device to pull apart the foil tapes in different directions.

8. The test magazine of claim 7, characterized in that the tape tensioning device has two deflecting cylinders that can rotate in opposite directions or are stationary and are arranged laterally spaced apart from one another at a dispensing site, wherein the tape tensioning device has take-up spools for receiving the foil tape located downstream from the deflecting cylinders.

9. The test magazine of claim 6, further comprising:
   the transport means, wherein the transport means are in operative connection with a test unit.

10. The test magazine of claim 6, further comprising:
    the transport means, wherein the transport means comprise a handling device to pick up and position a lancing unit that has been exposed by pulling apart the foil tapes at a dispensing position.

11. The test magazine of claim 10, characterized in that at least one of the foil tapes has positioning holes especially in the region of the holding cells for the test units to enable the handling device to engage.

12. The test magazine of claim 6, characterized in that the lancing units are physically joined to the test units as integrated test elements.

13. The test magazine of claim 6, characterized in that at least one of the foil tapes is provided with a withdrawal structure for adhesive or clamping fixation of used lancing elements.

14. The test magazine of claim 6, characterized in that the lancing units are arranged flat between the foil tapes as flat material components.

15. The test magazine of claim 6, characterized in that the foil tapes have a planar design and rest laminarly against the lancing units free of blisters.

16. The test magazine of claim 6, characterized in that the lancing units exposed at a dispensing site can be redispensed at a return position on one of the foil tapes.

17. The test magazine of claim 6, characterized in that the lancing units are formed on the test units in order to transfer collected body fluid.

18. The test magazine of claim 6, characterized in that the holding cells are delimited by linear foil connections, including welded or adhesive seams between the foil tapes.

19. The test magazine of claim 18, characterized in that the holding cells are sealed against one another and against the environment in a material-tight manner by the foil connections.

20. The test magazine of claim 18, characterized in that the linear foil connections extend obliquely to the tape longitudinal direction of the foils.

21. The test magazine of claim 6, characterized in that the lancing units are immobilized in a fixed position in their assigned holding cell by form-locking bordering foil connections or foil connections that engage in recesses.

22. The test magazine of claim 6, characterized in that at least one of the foil tapes has or forms a transparent measuring window for an optical measurement of the test units.

23. The test magazine of claim 6, characterized in that the foil tapes containing the test elements are held ready as a folded package in a zigzag folding.

24. The test magazine of claim 6, characterized by a cassette that receives the foil tapes with the test elements located therein.

25. The test magazine of claim 24, characterized in that the cassette is designed as a dispenser for test elements such that the individually dispensed test elements can be used in a separate test device.

26. The test magazine of claim 6, characterized in that the test units are designed to detect an analyte in the body fluid.

27. The test magazine of claim 6, further comprising:
the transport means, wherein the transport means are in operative connection with a disposal site located on the foil tapes in order to return a lancing unit.

28. A test magazine, comprising:
at least two foil tapes joined together in a layered manner by foil connections, the foil connections sealing first and second holding cells from one another;
a plurality of lancing units arranged in the first holding cells;
a plurality of test units arranged in the second holding cells that are separately sealed by the foil connections from the lancing units in the first holding cells;
wherein first holding cells do not contain the test units and the second holding cells do not contain the lancing units; and
wherein the lancing units each have a semi-open capillary channel and a holding region connected to the semi-open capillary channel, the semi-open capillary channel having a groove shape for transferring blood to the holding region.

29. The test magazine of claim 28, characterized in that the lancing units and test units are arranged alternately in a tape direction or adjacent to one another in pairs at right angles to the tape direction in associated holding cells.

30. The test magazine of claim 28, characterized in that the lancing units in the holding cells were sterilized by irradiation through a mask in order to screen the test units.

31. The test magazine of claim 28, characterized in that the foil tapes are joined to a test tape over their length and that cells on the test tape are exposed by perforations in the foil tapes to form the test units.

32. The test magazine of claim 28, characterized in that a desiccant for the test units is stored in the holding cells.

33. The test magazine of claim 28, characterized in that the holding cells are delimited by linear foil connections, including welded or adhesive seams between the foil tapes.

34. The test magazine of claim 33, characterized in that the holding cells are sealed against one another and against the environment in a material-tight manner by the foil connections.

* * * * *